US010409959B2

(12) United States Patent
Takahama et al.

(10) Patent No.: US 10,409,959 B2
(45) Date of Patent: Sep. 10, 2019

(54) MEDICINE FILLING APPARATUS (71) Applicant: Takazono Technology Incorporated, Hirakata-shi, Osaka (JP)

(72) Inventors: Makio Takahama, Hirakata (JP); Hirotsugu Kanemoto, Hirakata (JP)

(73) Assignee: Takazono Technology Incorporated, Osaka (JP)

( * ) Notice: Subject to any disclaimer, the term of this patent is extended or adjusted under 35 U.S.C. 154(b) by 477 days.

(21) Appl. No.: 15/027,914

(22) PCT Filed: Oct. 9, 2013

(86) PCT No.: PCT/JP2013/077479
§ 371 (c)(1),
(2) Date: Apr. 7, 2016

(87) PCT Pub. No.: WO2015/052797
PCT Pub. Date: Apr. 16, 2015

(65) Prior Publication Data
US 2016/0253474 A1 Sep. 1, 2016

(51) Int. Cl.
G06F 19/00 (2018.01)
A61J 7/00 (2006.01)
(Continued)

(52) U.S. Cl.
CPC ........ *G06F 19/3456* (2013.01); *A61J 7/0084* (2013.01); *B65B 5/103* (2013.01);
(Continued)

(58) Field of Classification Search
CPC ... B65B 2039/009; B65B 35/08; B65B 37/08; B65B 39/007; B65B 57/14; B65B 57/20;
(Continued)

(56) References Cited

U.S. PATENT DOCUMENTS 3,722,740 A * 3/1973 List ................... B65G 47/1428
221/169
3,921,851 A * 11/1975 Nilson ............... B65D 83/0409
221/151
(Continued)

FOREIGN PATENT DOCUMENTS

CN 101128358 A 2/2008
CN 201058117 Y 5/2008
(Continued)

*Primary Examiner* — Andrew M Tecco
*Assistant Examiner* — Nicholas E Igbokwe
(74) *Attorney, Agent, or Firm* — The Webb Law Firm (57) ABSTRACT

Provided is a medicine filling apparatus used for filling a medicine container with solid medicines, including: a medicine housing unit configured to house the medicines and having a plurality of medicine outlets configured to eject the housed medicines; a rotor located within the medicine housing unit, having a plurality of temporary medicine housing units configured to temporarily house the medicines, and configured to move the medicines housed in the plurality of temporary medicine housing units to the plurality of medicine outlets by rotating; and a drive unit configured to rotationally drive the rotor, wherein when at least one of the temporary medicine housing units coincides with at least one of the medicine outlets so that the medicines can be ejected, the temporary medicine housing units and the medicine outlets that are not in coincidence with each other are shifted by an angle such that the medicines cannot be ejected.

3 Claims, 6 Drawing Sheets (51) Int. Cl.
   *B65B 37/08* (2006.01)
   *B65B 39/00* (2006.01)
   *G07F 11/44* (2006.01)
   *G07F 17/00* (2006.01)
   *B65B 35/08* (2006.01)
   *B65B 65/02* (2006.01)
   *B65B 57/14* (2006.01)
   *B65B 57/20* (2006.01)
   *B65B 5/10* (2006.01)

(52) U.S. Cl.
   CPC .............. *B65B 35/08* (2013.01); *B65B 37/08* (2013.01); *B65B 57/14* (2013.01); *B65B 57/20* (2013.01); *B65B 65/02* (2013.01); *G07F 11/44* (2013.01); *G07F 17/0092* (2013.01); *B65B 39/007* (2013.01); *B65B 2039/009* (2013.01)

(58) Field of Classification Search
   CPC ......... B65B 5/103; B65B 65/02; G07F 11/44; G07F 17/0092
   USPC ........................................ 53/237, 244, 247
   See application file for complete search history.

(56) References Cited

U.S. PATENT DOCUMENTS

| | | | | |
|---|---|---|---|---|
| 5,803,309 | A * | 9/1998 | Yuyama | G07F 17/0092 221/27 |
| 5,927,546 | A * | 7/1999 | Yuyama | B65G 47/1457 221/265 |
| 6,170,229 | B1 * | 1/2001 | Kim | B65B 35/56 221/265 |
| 6,253,953 | B1 | 7/2001 | Ishizuka | |
| 6,394,308 | B1 * | 5/2002 | Yuyama | B65G 47/1457 221/265 |
| 7,131,554 | B2 * | 11/2006 | Hashimoto | B65B 5/103 221/197 |
| 7,562,791 | B2 | 7/2009 | Yuyama et al. | |
| 7,669,733 | B2 * | 3/2010 | Kim | G07F 11/54 221/261 |
| 9,038,816 | B2 | 5/2015 | Koike et al. | |
| 9,238,555 | B2 | 1/2016 | Koike et al. | |
| 2008/0164281 | A1 | 7/2008 | Yuyama et al. | |
| 2010/0078445 | A1 * | 4/2010 | Nam | B65B 35/08 221/154 |
| 2011/0042404 | A1 * | 2/2011 | Koike | G07F 9/026 221/2 |
| 2013/0256097 | A1 | 10/2013 | Koike et al. | |
| 2015/0224030 | A1 | 8/2015 | Koike et al. | |

FOREIGN PATENT DOCUMENTS

| | | |
|---|---|---|
| CN | 103108619 A | 5/2013 |
| JP | 624401 A | 2/1994 |
| JP | 7165202 A | 6/1995 |
| JP | 10258801 A | 9/1998 |
| JP | 119664 A | 1/1999 |
| JP | 200426311 A | 1/2004 |
| JP | 2006151451 A | 6/2006 |
| JP | 2013154915 A | 8/2013 |

* cited by examiner

MEDICINE FILLING APPARATUS

CROSS-REFERENCE TO RELATED APPLICATION

This application is the United States national phase of International Application No. PTC/JP2013/077479 filed Oct. 9, 2019, the disclosure of which is hereby incorporated in its entirely by reference.

FIELD

The present invention relates to a medicine filling apparatus used for filling a medicine container with solid medicines.

BACKGROUND

A pharmacist may provide a patient with solid medicines such as tablets according to a prescription by a doctor. In order to provide the patient with the medicines, the pharmacist may package the medicines separately by the type and amount of one-time dose (separate package) in some cases, or the pharmacist may fill a medicine container such as a vial container with the medicines collectively in other cases.

As an apparatus for filling a vial container with medicines, a tablet packing apparatus disclosed in JP H10-258801 A (Patent Literature 1), for example, can be mentioned. The tablet packing apparatus includes a tablet feeder capable of delivering tablets in an amount according to the prescription to the vial container. The tablet feeder includes a housing body that houses tablets, and a rotor rotatably located within the housing body. As the rotor rotates, the tablets can be sequentially ejected from an outlet provided in the housing body. The ejected tablets are delivered to the vial container after being counted by a tablet passage sensor provided in the tablet packing apparatus. In the configuration disclosed in Patent Literature 1, an outlet is provided at one point per unit of tablet feeder.

The vial container is filled with a lot of tablets. Therefore, in order to reduce the time required for filling operation, the rotor needs to rotate at high speed.

However, when the rotor rotates at high speed, there is a possibility of failure of filling in an exact quantity due to the tablets jamming within the tablet feeder or counting errors occurring in the tablet passage sensor.

JP H7-165202 A (Patent Literature 2) discloses providing outlets at two points for one unit of tablet feeder. However, in the configuration disclosed in Patent Literature 2, separate packing apparatuses are connected to the respective outlets. Therefore, in attempts to rotate the rotor at high speed for reducing the time required for filling operation, filling in an exact quantity may be failed due to the tablets jamming within the tablet feeder or counting errors occurring in the tablet passage sensor, like in the configuration of Patent Literature 1.

CITATION LIST

Patent Literature

Patent Literature 1: JP H10-258801 A
Patent Literature 2: JP H7-165202 A

SUMMARY

Technical Problem

It is therefore an object of the present invention to provide a medicine filling apparatus capable of reducing the time required for filling operation and filling a medicine container with medicines in an exact quantity.

Solution to Problem

The present invention is a medicine filling apparatus used for filling a medicine container with solid medicines, including: a medicine housing unit configured to house the medicines and having a plurality of medicine outlets configured to eject the housed medicines; a rotor located within the medicine housing unit, having a plurality of temporary medicine housing units configured to temporarily house the medicines, and configured to move the medicines housed in the plurality of temporary medicine housing units to the plurality of medicine outlets by rotating; a medicine guide path configured to guide the medicines ejected from the plurality of medicine outlets to the medicine container; and a drive unit configured to rotationally drive the rotor, wherein when at least one of the temporary medicine housing units coincides with at least one of the medicine outlets so that the medicines can be ejected, the temporary medicine housing units and the medicine outlets that are not in coincidence with each other are shifted by an angle such that the medicines cannot be ejected.

Further, the configuration may be such that the plurality of temporary medicine housing units are formed along the rotation direction of the rotor at equal intervals, the plurality of medicine outlets are formed along the rotation direction of the rotor at intervals different from those of the plurality of temporary medicine housing units, and when the at least one of the temporary medicine housing units coincides with the at least one of the medicine outlets, with the rotation of the rotor, so that the medicines can be ejected, the angle at which the temporary medicine housing units and the medicine outlets that are not in coincidence with each other are shifted is an integer multiple of an angle obtained by dividing an angle corresponding to each of the intervals at which the plurality of temporary medicine housing units are formed by the number of the plurality of medicine outlets formed.

Further, the number of the plurality of temporary medicine housing units formed may be larger than the number of the plurality of medicine outlets formed.

Further, the plurality of temporary medicine housing units may be recesses that are recessed in the radially inward direction from the outer circumferential edge of the rotor.

DESCRIPTION OF EMBODIMENT

Next, the present invention is described with reference to an embodiment of a medicine filling apparatus. The medicine filling apparatus includes a medicine cassette 1 as a medicine housing unit, a drive unit 2, a control unit (not shown), a medicine guide path 4, a medicine container arranging unit 5, and a medicine passage sensor 6 as a detection unit.

Figure 4:
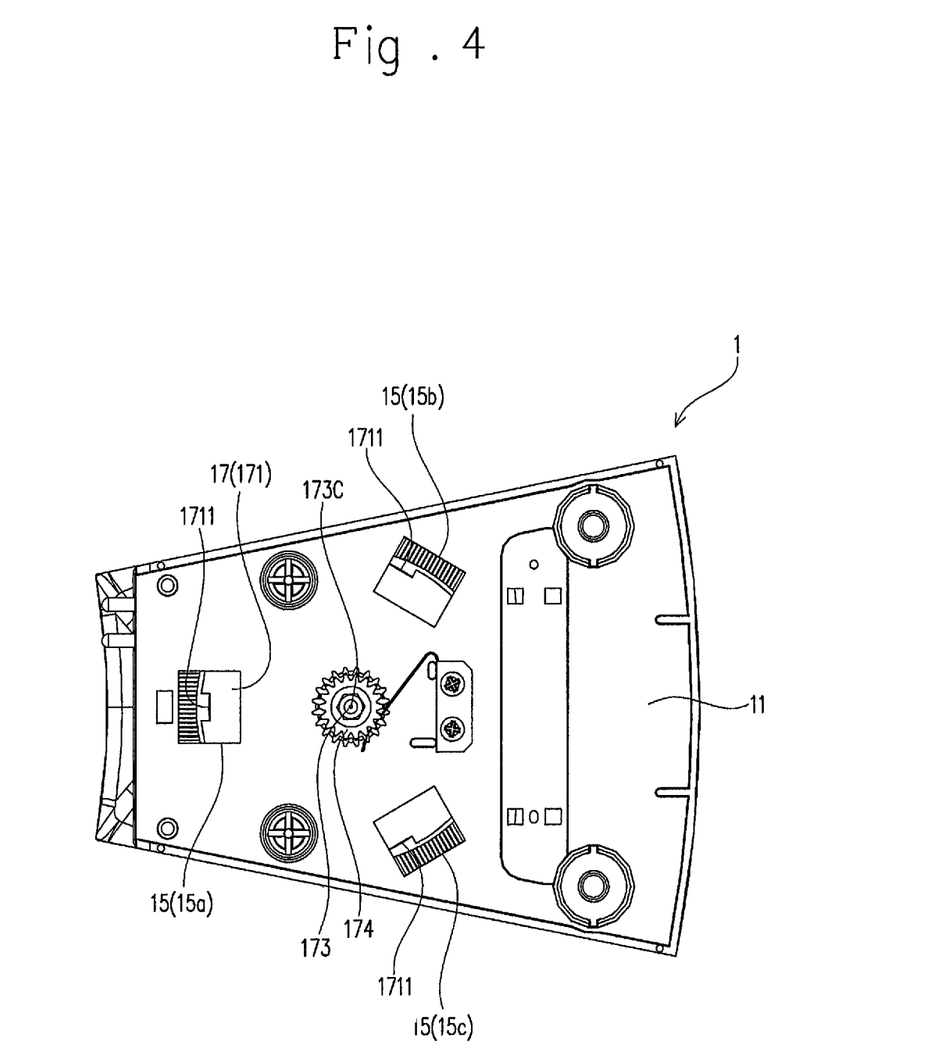
FIG. 4 is a bottom view showing the medicine housing unit used for the medicine filling apparatus.

The medicine cassette 1, which corresponds to the tablet feeder disclosed in Patent Literatures 1 and 2 above, is in the form of a box made of resin or the like, and can house a plurality of tablets M and appropriately eject them. As shown in FIG. 4, the medicine cassette 1 of this embodiment is substantially trapezoidal, as viewed from the bottom. The medicine cassette 1 is replaceable on a base (not shown) provide in the body of the medicine filling apparatus. The medicine cassette 1 houses a single kind of tablets M.

Figure 1:
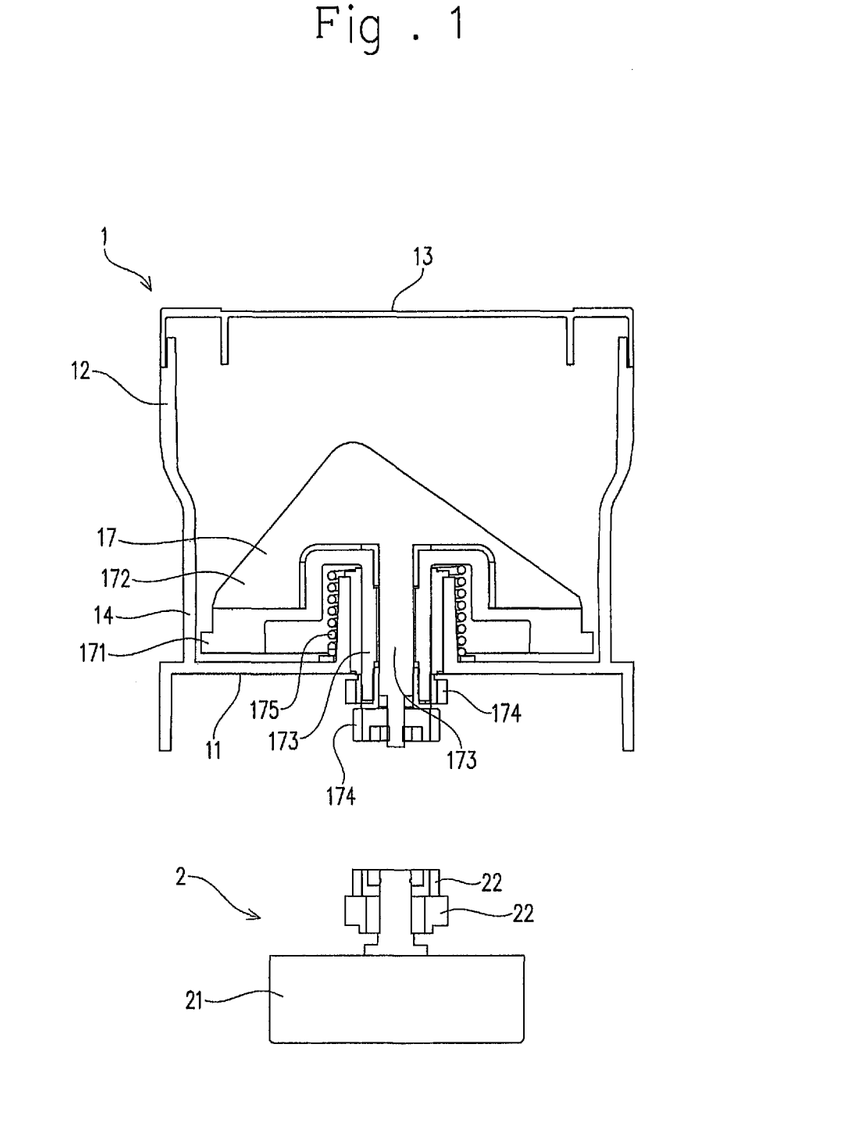
FIG. 1 is a vertical end face view in the width direction showing a medicine housing unit used for a medicine filling apparatus according to an embodiment of the present invention.
Figure 2:
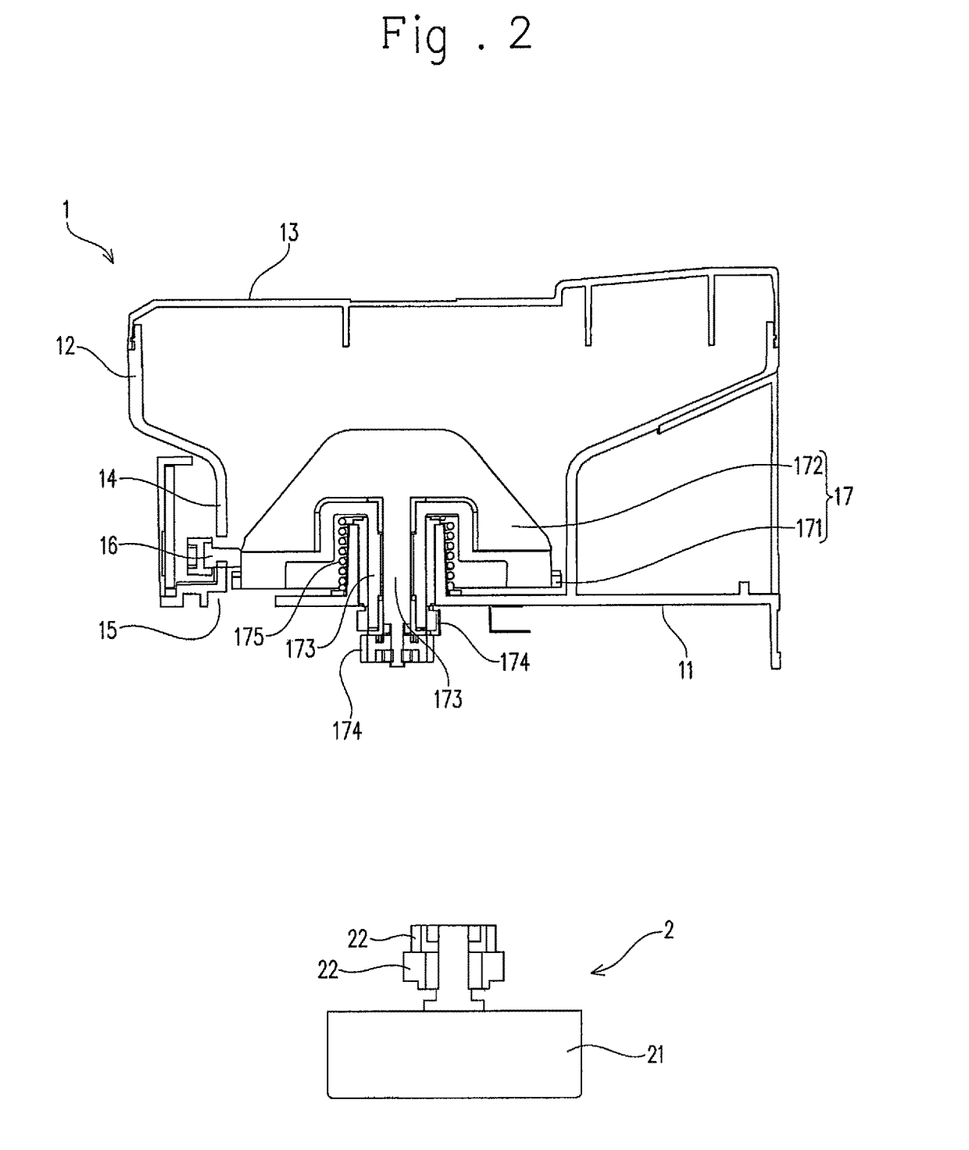
FIG. 2 is a vertical end face view in the depth direction showing the medicine housing unit used for the medicine filling apparatus.

As shown in FIG. 1 and FIG. 2, the medicine cassette 1 has a bottom wall 11 and side walls 12 raised upward from the bottom wall 11, and a cover 13 is detachably attached onto the top of the side walls 12. Further, a cylindrical part 14 having an inner circumferential surface with a diameter slightly larger than the outer diameter of a lower disk part 171 of a rotor 17 is formed on the bottom wall 11. The rotor 17 is located inside the cylindrical part 14. One rotor 17 is provided in the medicine cassette 1 of this embodiment.

Figure 6:
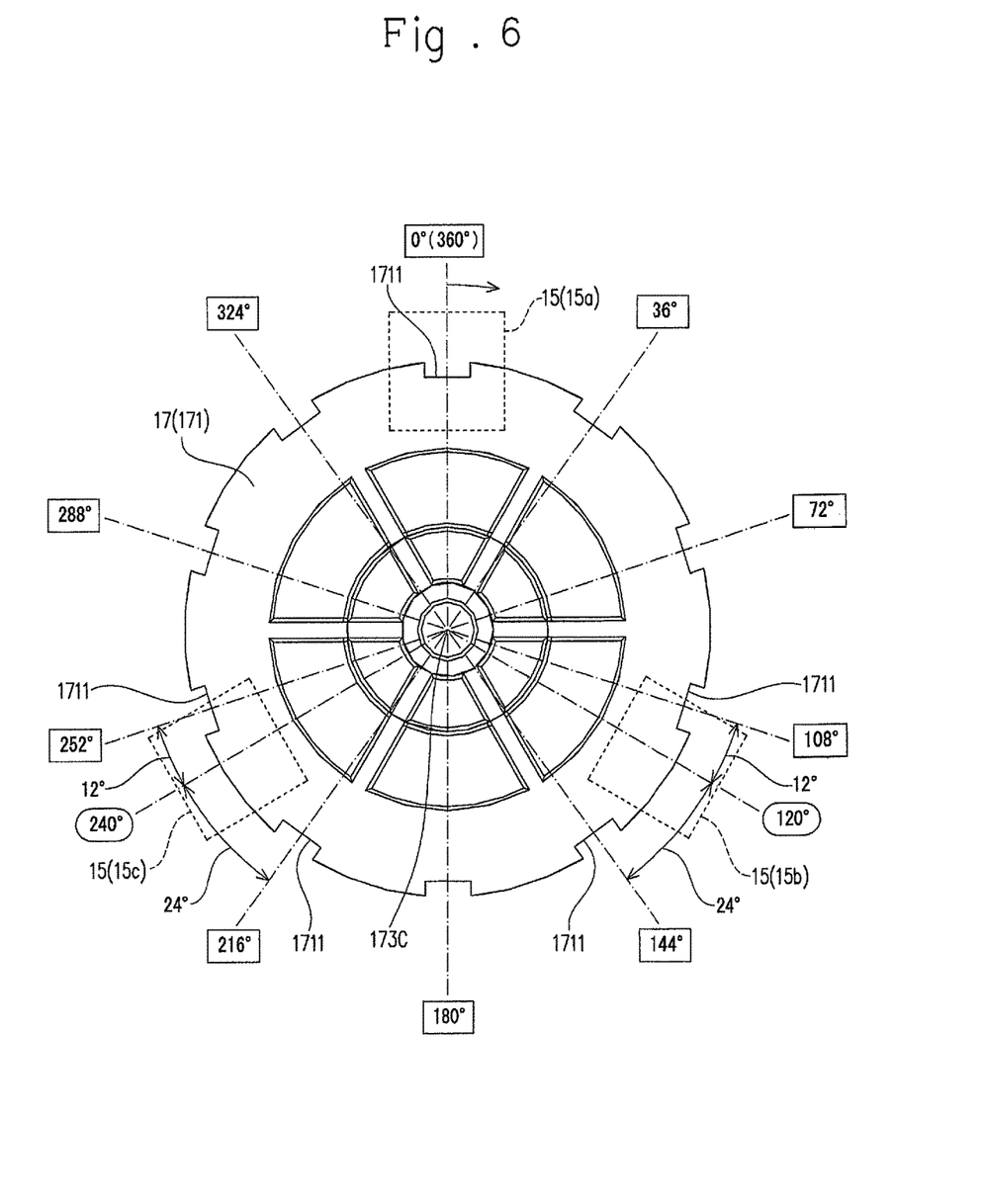
FIG. 6 is a schematic view showing the positional relationship between medicine housing recesses and medicine outlets in the rotor of the medicine housing unit used for the medicine filling apparatus.

A plurality of medicine outlets 15 are formed in a portion on the bottom wall 11 that is surrounded by the cylindrical part 14, more specifically, a portion adjacent to the inner circumferential surface of the cylindrical part 14. As shown in FIG. 6, the medicine outlets 15 are formed at three points at equal intervals each at an angle of 120° with reference to a vertical axis 173C.

As shown in FIG. 2, a partition plate 16 extending in the horizontal direction is provided above each of the medicine outlets 15 so as to project in the radially inward direction from the inner circumferential surface of the cylindrical part 14. The partition plate 16 covers over the medicine outlet 15, thereby preventing two or more tablets M from falling into the medicine outlet 15 at a time. In the medicine cassette 1 of this embodiment, the medicine outlets 15 are formed at three points, and therefore partition plates 16 are also provided at three points.

Further, the rotor 17 configured to rotate about the vertical axis 173C (see FIG. 4) is provided on the bottom wall 11 of the medicine cassette 1. A rotation shaft 173 of the rotor 17 passes through the bottom wall 11. The rotation shaft 173 is provided with a driven gear 174 to which a driving force for rotationally driving the rotor 17 is transmitted from the drive unit 2 below the bottom wall 11. Further, the rotor 17 is biased upward by a spring 175.

Figure 3:
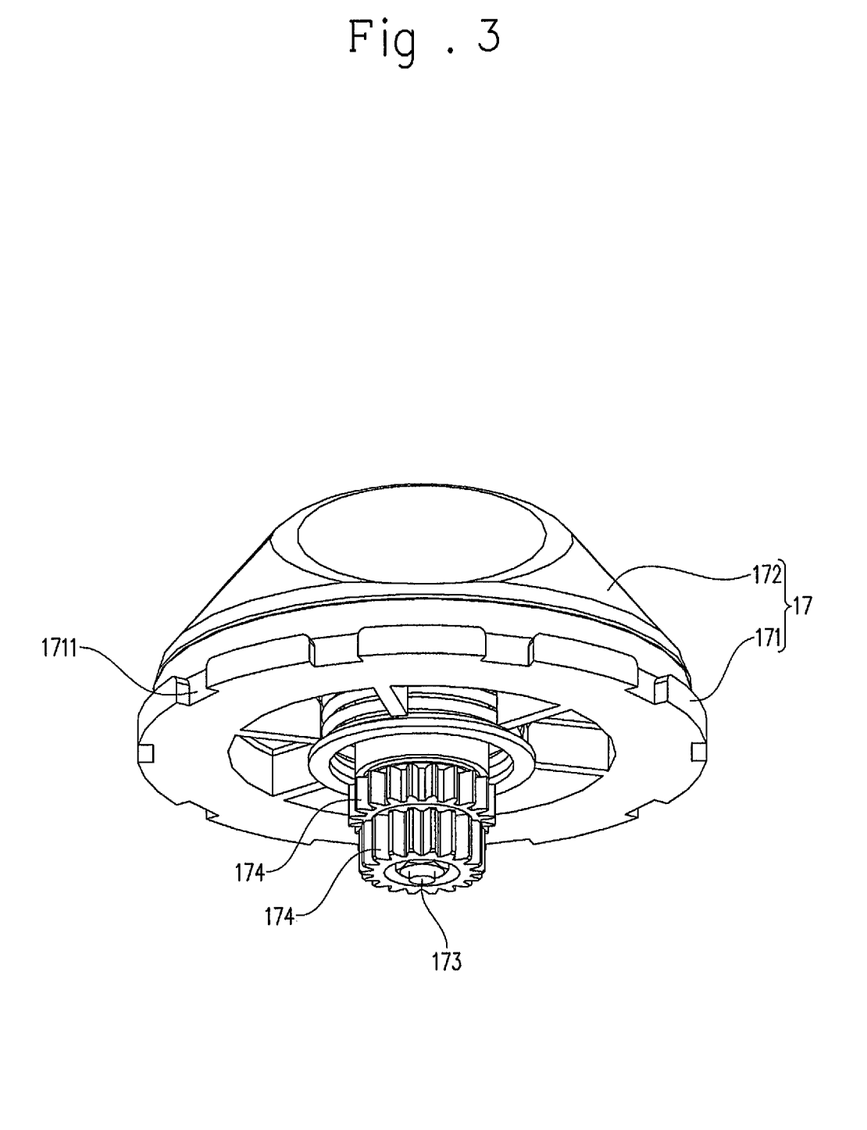
FIG. 3 is a perspective view showing a rotor of the medicine filling apparatus.

As shown in FIG. 3, the rotor 17 includes the lower disk part 171 and an upper bulging part 172. Although the lower disk part 171 and the upper bulging part 172 are separate and are configured to rotate separately in this embodiment, they may be integrated. In order to allow the lower disk part 171 and the upper bulging part 172 to rotate separately, the rotation shaft 173 includes inner and outer double shafts, and the driven gear 174 is provided for each shaft.

The upper bulging part 172 has a shape rising upward at a radially inward position and has a surface inclined toward a radially outward position. This shape allows the tablets M to slip down on the inclined surface, so that the tablets M housed in the medicine cassette 1 can be smoothly introduced downward. The lower disk part 171 has a substantially circular cross section, in which medicine housing recesses 1711 serving as temporary medicine housing units are formed along the rotation direction of the rotor 17 evenly at 10 points (at equal intervals at an angle of 36° with reference to the vertical axis 173C) so as to be recessed in the radially inward direction. Therefore, the plurality of medicine outlets 15 are formed along the rotation direction of the rotor 17 evenly at intervals different from those of the plurality of medicine housing recesses 1711. The number of the temporary medicine housing units 1711 formed (10 points) is larger than the number of the medicine outlets 15 formed (three points).

The tablets M are fitted into the respective medicine receiving recesses 1711. With such a state, the rotor 17 rotates. Therefore, the rotor 17 can rotate while the plurality of tablets M are temporarily housed in the medicine housing recesses 1711. Since the partition plates 16 prevent two or more tablets M from falling into the respective medicine outlets 15 at a time, the tablets M move (fall) into the respective medicine outlets 15 one by one, as the rotor 17 rotates with the tablets M being fitted into the medicine receiving recesses 1711. The relationship between the medicine housing recesses 1711 and the medicine outlets 15 will be described later.

The drive unit 2 is located in the base (not shown) provided in the body of the medicine filling apparatus. As shown in FIG. 1 and FIG. 2, the drive unit 2 includes a motor 21 as a driving source, and a drive gear 22 as a power transmission mechanism to which a driving force is transmitted from the motor 21. The drive gear 22 meshes with the driven gear 174 of the medicine cassette 1 when the medicine cassette 1 is attached to the body of the medicine filling apparatus. The drive unit 2 is controlled by the control unit so as to rotate the rotor 17 and stop the rotation. The medicines can be ejected from the medicine cassette 1 to the medicine guide path 4 by the drive unit 2.

Figure 5:
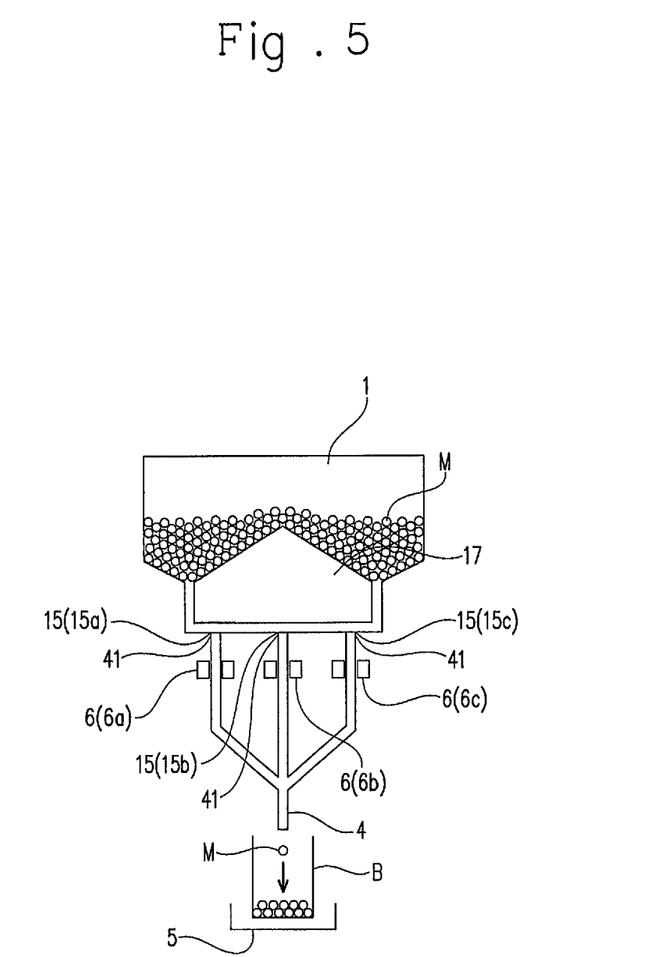
FIG. 5 is a schematic view showing the configuration of the medicine filling apparatus.

The medicine guide path 4 is located in the body of the medicine filling apparatus and is a path connecting the medicine outlets 15 (15*a* to 15*c*) of the medicine cassette 1 to the medicine container arranging unit 5 in which a medicine container B such as a vial container is arranged, as shown in FIG. 5. The medicines ejected from the medicine cassette 1 move to the opening of the medicine container B passing through the medicine guide path 4. The medicine guide path 4 has a plurality of (three) inlets 41 located corresponding to the medicine outlets 15 (15*a* to 15*c*) of the medicine housing unit. Further, an outlet 42 that is open into the medicine container B is provided at one point.

As shown in FIG. 5, a medicine passage sensor 6 serving as the detection unit configured to detect the tablets M passing therethrough is provided in a portion of the medicine guide path 4 located in the base (not shown) provided in the body of the medicine filling apparatus. The detection signals of the medicine passage sensor 6 are sent to the control unit to be processed. A first medicine passage sensor 6*a* is provided corresponding to the first medicine outlet 15*a*, a second medicine passage sensor 6*b* is provided corresponding to the second medicine outlet 15*b*, and a third medicine passage sensor 6*c* is provided corresponding to the third medicine outlet 15*c*. The medicine passage sensors 6 (6*a* to 6c) respectively detect the tablets M ejected from the medicine outlets 15 (15a to 15c).

As described above, the plurality of medicine outlets 15 are formed on the bottom wall 11 of the medicine cassette 1. The plurality of medicine housing recesses 1711 are formed in the lower disk part 171 of the rotor 17. With the rotation of the rotor 17, one of the plurality of medicine housing recesses 1711 coincides with one of the plurality of medicine outlets 15. In this regard, the plurality of medicine housing recesses 1711 and the plurality of medicine outlets 15 are arranged so that, even if any one of the plurality of medicine housing recesses 1711 coincides with any one of the plurality of medicine outlets 15, the residual medicine housing recesses 1711 except the one do not coincide with the residual medicine outlets 15 except the one.

In this embodiment, the plurality of medicine housing recesses 1711 are arranged along the rotation direction of the rotor 17 at equal intervals. The plurality of medicine outlets 15 are arranged along the rotation direction of the rotor 17 at intervals. The medicine outlets 15 each have a different shift angle (with reference to the vertical axis 173C) to the closest medicine housing recess 1711 on the upstream side in the rotation direction of the rotor 17. Further, when one of the plurality of medicine housing recesses 1711 coincides with one of the plurality of medicine outlets 15, the residual medicine outlets 15 except the one are shifted by an integer multiple of a specific angle to the closest medicine housing recess 1711 on the upstream side in the rotation direction of the rotor 17. The specific angle is an angle obtained by dividing the angle corresponding to each of the equal intervals of the plurality of medicine housing recesses 1711 (with reference to the vertical axis 173C) by the number of the plurality of medicine outlets 15 formed.

Specifically, the medicine outlets 15 are formed at three points on the bottom wall 11 of the medicine cassette 1, as described above. Further, the medicine housing recesses 1711 are formed at 10 points in the lower disk part 171 of the rotor 17. The positional relationship of the medicine housing recesses 1711 to one of the medicine outlets 15 following the rotation of the rotor 17 is as follows. That is, as shown in FIG. 4 and FIG. 6, when one of the medicine housing recesses 1711 coincides with one of the medicine outlets 15 (15a), with the rotation of the rotor 17, so that the tablets M can be ejected, the temporary medicine housing units 1711 except the one are shifted from the medicine outlets 15 (15b and 15c) except the one by an angle such that the tablets M cannot be ejected.

The shift angle is an integer multiple of an angle (an angle of 12° with reference to the vertical axis 173C) obtained by dividing the angle (an angle of 36° with reference to the vertical axis 173C) corresponding to each of the intervals at which the plurality of medicine housing recesses 1711 are formed by the number (three (points)) of the plurality of medicine outlets 15 formed. Specifically, of the medicine outlets 15 (15b and 15c) except the one, the medicine outlet 15b located on the right side in FIG. 6 has angles of 12° in the counterclockwise direction (12° multiplied by one) and 24° (12° multiplied by two) in the clockwise direction, with respect to the medicine housing recesses 1711 at two points that are located at positions with the center in the circumferential direction of the medicine outlet 15b interposed.

Further, the medicine outlet 15c located on the left side in FIG. 6 has distances at positions of 24° (12° multiplied by two) in the counterclockwise direction and 12° (12° multiplied by one) in the clockwise direction, with respect to the medicine housing recesses 1711 at two points that are located at positions with the center in the circumferential direction of the medicine outlet 15c interposed.

The medicine outlets 15 at three points and the medicine housing recesses 1711 at 10 points are formed so as to have such shift angles, thereby allowing the tablets M to be sequentially ejected from the medicine outlets 15 at three points with one rotation of the rotor 17. That is, with one rotation of the rotor 17, 30 (10×3) tablets M are calculationally ejected from the medicine cassette 1. On the other hand, in a medicine housing unit (medicine cassette) provided with only a medicine outlet at one point, the tablets can be ejected from only the medicine outlet at one point with one rotation of the rotor. That is, only 10 tablets are ejected from the medicine cassette 1 with one rotation of the rotor. Therefore, in this embodiment, the tablets M can be calculationally ejected three times in the number, even at the same rotational speed of the rotor 17, and therefore high speed filling can be achieved at relatively low rotational speed.

Further, when one of the medicine housing recesses 1711 coincides with one of the medicine outlets 15 (15a), with the rotation of the rotor 17, so that the tablets M can be ejected, the temporary medicine housing units 1711 except the one are shifted from the medicine outlets 15 (15b and 15c) except the one so that the tablets M cannot be ejected. Therefore, at the moment when the tablets M are ejected from the one of the medicine outlets 15 (15a), the tablets M are not ejected from the medicine outlets 15 (15b and 15c) except the one. That is, the tablets M can never be ejected simultaneously from the medicine outlets 15 at three points, and therefore the tablets M can be counted one by one based on the detection by the medicine passage sensor 6.

Hereinbefore, an embodiment of the present invention has been described. However, the present invention is not limited to the above described embodiment, and various modifications can be made without departing from the gist of the present invention.

For example, the medicines serving as objects with which the medicine container B is filled are not limited to tablets, and the present invention can be applied generally to solid medicines such as capsules. Further, the medicines are not limited to the prescription medicines and may be medicines that do not need a prescription by a doctor. Further, the "medicines" are not limited to those having medicinal properties and include solid nutritional supplements (supplements), for example. Further, the numbers of the medicine outlets 15 and the temporary medicine housing units 1711 to be formed are not limited to those in this embodiment (three points of the medicine outlets 15 and 10 points of the temporary medicine housing units 1711), and various numbers of them can be formed. The number of the medicine outlets 15 formed can be optionally selected, for example, within the range of 2 points to 4 points. The number of the medicine housing recesses 1711 formed can be optionally selected, for example, within the range of 5 points to 15 points. Further, the medicine outlets 15 are not limited to those formed at equal intervals as in this embodiment, and they can be formed at unequal intervals. Further, the temporary medicine housing units 1711 may coincide with the medicine outlets 15 simultaneously at two or more points so that the medicines can be ejected. Further, the detection unit (medicine passage sensor) 6 needs only to be capable of detecting the medicines passing through the medicine guide path 4, and is not limited to being provided in the medicine guide path 4. For example, the detection unit 6 can be provided in the medicine cassette 1. Further, one unit of the medicine cassette 1 can include two or more rotors 17.

Further, a plurality of medicine cassettes 1 can be attached to the body of the medicine filling apparatus. In this case, a plurality of inlets 41 of the medicine guide path 4 are located corresponding to the plurality of medicine cassettes 1. The lines of the medicine guide path 4 merge in the middle, and the outlet 42 that is open into the medicine container B is located at one point. However, for the purpose of contamination prevention or the like, it is possible that not all the lines of the medicine guide path 4 merge in the middle, and outlets 42 are provided at two or more points in the medicine guide path 4.

Finally, the configuration and action of this embodiment will be summarized. This embodiment is a medicine filling apparatus used for filling a medicine container B with solid medicines (tablets) M, the medicine filling apparatus including: a medicine housing unit (medicine cassette) 1 configured to house the medicines (tablets) M and having a plurality of medicine outlets 15 configured to eject the housed medicines (tablets) M; a rotor 17 located within the medicine housing unit (medicine cassette) 1, having a plurality of temporary medicine housing units (medicine housing recesses) 1711 configured to temporarily house the medicines (tablets) M, and configured to move the medicines (tablets) M housed in the plurality of temporary medicine housing units (medicine housing recesses) 1711 to the plurality of medicine outlets 15 by rotating; a medicine guide path 4 configured to guide the medicines (tablets) M ejected from the plurality of medicine outlets 15 to the medicine container; and a drive unit 2 configured to rotationally drive the rotor 17, wherein when at least one of the temporary medicine housing units (medicine housing recesses) 1711 coincides with at least one of the medicine outlets 15 so that the medicines can be ejected, the temporary medicine housing units (medicine housing recesses) 1711 and the medicine outlets 15 that are not coincidence with each other are shifted by an angle such that the medicines cannot be ejected.

According to this configuration, when the one of the temporary medicine housing units (medicine housing recesses) 1711 coincides with the one of the medicine outlets 15, with the rotation of the rotor 17, so that the medicines can be ejected, the temporary medicine housing units (medicine housing recesses) 1711 except the one are shifted from the medicine outlets 15 except the one so that the medicines cannot be ejected. In this configuration, the medicines (tablets) M can be ejected from the plurality of medicine outlets 15 with one rotation of the rotor 17. On the other hand, in a medicine housing unit (medicine cassette) provided with only a medicine outlet at one point, the medicines (tablets) M can be ejected from only the medicine outlet at one point with one rotation of the rotor 17. Therefore, in this embodiment, high speed filling can be achieved at relatively low rotational speed. Further, the medicines (tablets) M are not ejected simultaneously from the plurality of medicine outlets 15. Therefore, the medicines (tablets) M can be reliably counted one by one. Accordingly, jamming of the medicines (tablets) M within the medicine housing unit (medicine cassette) 1 or the occurrence of counting errors by the medicine passage sensor 6 can be suppressed.

Further, the configuration may be such that the plurality of temporary medicine housing units (medicine housing recesses) 1711 are formed along the rotation direction of the rotor 17 at equal intervals, the plurality of medicine outlets 15 are formed along the rotation direction of the rotor 17 at intervals different from those of the plurality of temporary medicine housing units (medicine housing recesses) 1711, and when the at least one of the temporary medicine housing units (medicine housing recesses) 1711 coincides with the at least one of the medicine outlets 15, with the rotation of the rotor 17, so that the medicines can be ejected, the angle at which the temporary medicine housing units (medicine housing recesses) 1711 and the medicine outlets 15 that are not in coincidence with each other are shifted is an integer multiple of an angle obtained by dividing an angle corresponding to each of the intervals at which the plurality of temporary medicine housing units (medicine housing recesses) 1711 are formed by the number of the plurality of medicine outlets 15 formed.

Further, the configuration may be such that the number of the plurality of temporary medicine housing units (medicine housing recesses) 1711 formed is larger than the number of the plurality of medicine outlets 15 formed.

Further, the configuration may be such that the plurality of temporary medicine housing units (medicine housing recesses) 1711 are recesses that are recessed in the radially inward direction from the outer circumferential edge of the rotor 17.

As described above, in the medicine filling apparatus according to this embodiment, high-speed filling at relatively low rotational speed is enabled, and therefore jamming of the medicines (tablets) M within the medicine housing unit (medicine cassette) 1 or the occurrence of counting errors by the medicine passage sensor 6 can be suppressed. Therefore, the time required for filling operation can be reduced, and the medicine container B can be filled with the medicines (tablets) M in an exact quantity.

REFERENCE SIGNS LIST

1: Medicine housing unit, Medicine cassette
15: Medicine outlet
17: Rotor
1711: Temporary medicine housing unit, Medicine housing recess
2: Drive unit
4: Medicine guide path
B: Medicine container
M: Medicines, Tablets

The invention claimed is:
1. A medicine filling apparatus used for filling a medicine container with solid medicines, comprising:
   a medicine housing unit configured to house the medicines and having a plurality of medicine outlets configured to eject the housed medicines;
   a rotor located within the medicine housing unit, having a plurality of temporary medicine housing units configured to temporarily house the medicines, and configured to move the medicines housed in the plurality of temporary medicine housing units to the plurality of medicine outlets by rotating;
   a medicine guide path configured to guide the medicines ejected from the plurality of medicine outlets to the medicine container; and
   a drive unit configured to rotationally drive the rotor, wherein
   the plurality of temporary medicine housing units are formed along the rotation direction of the rotor at equal intervals,
   the plurality of medicine outlets are formed along the rotation direction of the rotor at intervals different from those of the plurality of temporary medicine housing units, when the temporary medicine housing units and the medicine outlets are not in coincidence with each other, the medicines are not ejected from the medicine outlets, only when the temporary medicine housing units and the medicine outlets are in coincidence with each other, the medicines are ejected from the medicine outlets, and only one of the temporary medicine housing units is allowed to be in coincidence with only one of the medicine outlets to thereby allow the medicines to be ejected therefrom so that the medicines are prevented from being ejected from the plurality of medicine outlets at a time.

2. The medicine filling apparatus according to claim 1, wherein when the only one of the temporary medicine housing units and the only one of the medicine outlets are in coincidence with each other, with the rotation of the rotor, so that the medicines can be ejected, the angle at which the temporary medicine housing units that are not in coincidence with the only one of the medicine outlets and the medicine outlets that are not in coincidence with the only one of the temporary medicine housing units are shifted is an integer multiple of an angle obtained by dividing an angle corresponding to each of the intervals at which the plurality of temporary medicine housing units are formed by the number of the plurality of medicine outlets formed.

3. The medicine filling apparatus according to claim 2, wherein the number of the plurality of temporary medicine housing units formed is larger than the number of the plurality of medicine outlets formed.

* * * * *

UNITED STATES PATENT AND TRADEMARK OFFICE
CERTIFICATE OF CORRECTION

PATENT NO. : 10,409,959 B2
APPLICATION NO. : 15/027914
DATED : September 10, 2019
INVENTOR(S) : Makio Takahama et al.

It is certified that error appears in the above-identified patent and that said Letters Patent is hereby corrected as shown below:

In the Specification

Column 1, Line 7, delete "Iternational" and insert -- International --

Column 1, Line 7, delete "PTC/JP2013/077479" and insert -- PCT/JP2013/077479 --

Column 1, Line 8, delete "2019," and insert -- 2013, --

Column 1, Line 9, delete "entirely" and insert -- entirety --

Signed and Sealed this
Third Day of December, 2019

Andrei Iancu
*Director of the United States Patent and Trademark Office*